(12) United States Patent
Aoyagi (10) Patent No.: US 7,927,814 B2
(45) Date of Patent: Apr. 19, 2011

(54) ANTIBODY DIRECTED AGAINST GASTRIN-RELEASING PEPTIDE PRECURSOR AND USE THEREOF

(75) Inventor: Katsumi Aoyagi, Saitama (JP)

(73) Assignee: Advanced Life Science Institute, Inc., Saitama (JP)

( * ) Notice: Subject to any disclaimer, the term of this patent is extended or adjusted under 35 U.S.C. 154(b) by 120 days.

(21) Appl. No.: 11/974,820

(22) Filed: Oct. 15, 2007

(65) Prior Publication Data

US 2008/0182281 A1 Jul. 31, 2008

Related U.S. Application Data

(63) Continuation of application No. PCT/JP2006/307808, filed on Apr. 13, 2006.

(30) Foreign Application Priority Data

Apr. 13, 2005 (JP) .................................. 2005-115782

(51) Int. Cl.
| | |
|---|---|
| C12Q 1/00 | (2006.01) |
| G01N 33/00 | (2006.01) |
| G01N 33/48 | (2006.01) |
| G01N 33/53 | (2006.01) |
| G01N 33/566 | (2006.01) |
| G01N 33/567 | (2006.01) |
| G01N 33/574 | (2006.01) |

(52) U.S. Cl. ............ 435/7.1; 435/4; 435/7.21; 435/7.23; 435/7.92; 435/7.94; 436/63; 436/501; 436/503; 436/536

(58) Field of Classification Search .......................... None
See application file for complete search history.

(56) References Cited

U.S. PATENT DOCUMENTS 6,504,010 B1 * 1/2003 Wang et al. .................... 530/350

FOREIGN PATENT DOCUMENTS

| EP | 0 811 683 | 12/1997 |
|---|---|---|
| WO | WO 03/097666 | * 11/2003 |

OTHER PUBLICATIONS

Miyake et al., Cancer Research, 54:2136-2140 (1994).
Kodama et al., The Journal of Medicine, 32(1):87-97 (1994).

* cited by examiner

*Primary Examiner* — Alana M Harris
(74) *Attorney, Agent, or Firm* — Peter F. Corless; Christine C. O'Day; Edwards Angell Palmer & Dodge LLP

(57) ABSTRACT

Disclosed is a novel method for determination of ProGRP which is free from problems such as the dispersion in the values of measurements and operational constraints such as handling of a test sample. A method for the determination of a gastrin-releasing peptide precursor or a digest thereof using at least two different antibodies each of which can recognize a peptide comprising the partial amino acid sequence starting from amino acid residue 40 and ended at amino acid residue 75 in the amino acid sequence depicted in SEQ ID NO:1; and a method for the determination of a gastrin-releasing peptide precursor and/or a digest thereof using at least two different antibodies each of which can recognize a peptide comprising the partial amino acid sequence starting from amino acid residue 40 and ended at amino acid residue 79 in the amino acid sequence depicted in SEQ ID NO:1. The methods have such advantages that a detection sensitivity comparable to that in a conventional determination method can be achieved, that it is easy to handle a sample after the sample is collected, and that a highly reproducible measurements can be obtained.

5 Claims, 2 Drawing Sheets

Figure 2 ies including small cell lung cancer.
ANTIBODY DIRECTED AGAINST GASTRIN-RELEASING PEPTIDE PRECURSOR AND USE THEREOF This application is a continuation of International Application PCT/JP2006/307808 having an International filing date of Apr. 13, 2006, which in incorporated herein by reference in its entirety.

TECHNICAL FIELD

The present invention relates to an antibody directed against gastrin-releasing peptide precursor and use thereof, and is widely used in early diagnoses, monitoring of the treatment, monitoring of recurrence, or the like of various diseases including small cell lung cancer.

BACKGROUND ART

The most frequent cause of death in our country is malignant neoplasm, and in particular, the mortality of lung cancer in men is the highest, exceeding that of stomach cancer, while the mortality is the third highest in women and tends to be increasing every year. Lung cancer is histopathologically classified into the following four main subtypes, namely, squamous-cell carcinoma and small-cell lung carcinoma (SCLC) occurring in the hilar region, adenocarcinoma and large-cell lung carcinoma occurring in the lung field.

In particular, since small-cell lung carcinoma proliferates fast and causes remote metastasis in the early stage, it is often discovered, even on the initial diagnosis, to be progressive cancer in which metastasis has already occurred systemically. The cure rate of this type of cancer is approximately 20% for the patients with the limited disease (LD) type of small-cell lung carcinoma, in which pathological lesion is limited only to one side of the lung; however, for the patients with the extensive disease (ED) type in which cancer has metastasized to both lungs or to other organs, complete cure is said to be practically difficult.

Furthermore, since small-cell lung carcinoma is highly sensitive to anticancer drugs, chemotherapy is considered to be the best choice for the treatment of the disease. However, the rate of success with chemotherapy is low for non-small-cell lung carcinoma (non-SCLC), and thus surgical treatment is known to be the best choice for the treatment.

Therefore, small-cell lung carcinoma is a cancer which particularly necessitates early discovery and early treatment among lung cancers, and for this reason, differential diagnosis of small-cell lung carcinoma and non-small-cell lung carcinoma is extremely important for making decision on the course of treatment.

One of the methods for discovering lung cancer is sputum examination. However, although sputum examination is suitable predominantly for the examination of squamous-cell carcinoma, there is a problem that the positive rate for small-cell lung carcinoma is low. Also, X-ray imaging is another method widely used in the discovery of lung cancer; however, with regard to squamous-cell carcinoma or small-cell lung carcinoma which occurs in the hilar region, there is a problem that imaging of the shadow of cancerous tissues is very difficult because the shadow of the heart falls on the hilar region. Furthermore, with regard to small-cell lung carcinoma, it is believed that even though those patients who show anomalous shadow of the lung field are diagnosed using sputum cytodiagnosis, simple chest X-ray imaging, CT scanning, bronchoscopy and the like, early discovery of this type of lung cancer is never easy.

In addition, several examinations for diagnosing cancer, such as irradiation, biopsy and bronchoscopy, cause pain in patients, and require expensive instruments or skilled engineer.

Therefore, research is being conducted to find a tumor marker which enables highly efficient diagnosis of cancer at a curable stage through a more convenient blood examination method. Currently, 30 or more tumor markers are being used in the discovery and diagnosis of cancer patients, indication for monitoring of the course of disease, diagnosis of recurrence, or the like.

Since lung cancers have various subtypes, there is no report on a tumor marker which is effective in the discovery or diagnosis of all subtypes of lung cancer. Thus, at the present, effective tumor markers are selected and used in accordance with each subtype of lung cancer.

For example, carcinoembryonic antigen (CEA) or sialyl Lex-i antigen is mainly chosen and used for pulmonary adenocarcinoma, squamous-cell carcinoma related antigen (SCC) for squamous-cell carcinoma, and neuron-specific enolase (NSE) for small-cell lung carcinoma.

However, NSE is disadvantageous in that (1) the positive rate is low at an early, curable stage in SCLC; (2) a transient increase in the measured values is recognized upon treatment; (3) the measured values increase due to hemolysis during blood collection; (4) the difference in the measured values between small-cell lung carcinoma patients and normal persons is small; and the like. Thus, NSE could not necessarily be said to be an effective tumor marker for small-cell lung carcinoma.

Gastrin-releasing peptide (GRP) is a brain gut peptide comprising 27 amino acids, which was isolated from porcine stomach tissues by McDonald et al. in 1978, and has a gastrin secretion promoting effect. The presence of GRP in human has also been confirmed, and the gene encoding human GRP has been also cloned in 1984.

Yamaguchi et al. at the National Cancer Center in Japan measured 15 or more types of brain gut hormones, including adrenocorticotropic hormone (ACTH), calcitonin and the like, in the course of investigating the biological characteristics of small-cell lung carcinoma, which is conceived to be derived from neuroendocrine cells, and clarified that GRP is actively secreted from cultured small-cell lung carcinoma cell lines at the highest frequency and highest concentration (Non-Patent Document 1). Moreover, they also established a radioimmunoassay (RIA) combined with a method of concentrating GRP in blood, and found that patients with small-cell lung carcinoma would show higher blood concentration of GRP compared to normal persons. However, since GRP is rapidly digested in the blood, its concentration in blood is low, and since the aforementioned assay requires complicated concentration processes, clinical application is difficult.

From researches conducted thereafter, it was found that three species of GRP precursors (proGRP) are produced by alternative RNA splicing in various cells (Non-Patent Document 2). These three species of ProGRP show that the $1^{st}$ to $98^{th}$ amino acids in the amino acid sequence are common, while the amino acid sequence on and after the $99^{th}$ amino acid is different from each other, due to alternative RNA splicing. This common portion in the amino acid sequence of from the $1^{st}$ to $98^{th}$ amino acids, is shown in SEQ ID NO:1. Hereinafter, unless stated otherwise in particular, the numbering of amino acid residues in ProGRP according to the present invention, partial amino acid sequences thereof, digests and the like, is based on the numbering of the amino acid sequence of SEQ ID NO:1.

The amino acid sequence of from the 1$^{st}$ to 27$^{th}$ amino acids in the three species of ProGRP is identical to the amino acid sequence of mature GRP having gastrin secretion promoting activity. These three species of precursors are all digested by hormone precursor cleavage enzymes, into mature type GRP having an amino acid sequence consisting of amino acids 1-27, and a C-terminal fragment (ProGRP-Cfrag) which is a digest of ProGRP having an amino acid sequence from the 31$^{st}$ amino acid and the rest, and having no gastrin secretion promoting activity.

Holst et al. (Non-Patent Document 3) reported that in a radioimmunoassay (RIA) method using an anti-serum directed against a peptide having an amino acid sequence consisting of amino acids 42-53 of the amino acid sequence of ProGRP (hereinafter, referred to as ProGRP (42-53)), the level of ProGRP or ProGRP-Cfrag in plasma of the patients with small-cell lung carcinoma was high. However, in this method, precipitation and extraction processes were needed, and the sensitivity was insufficient. Furthermore, it is conceived that when immunization is carried out with such a short chain peptide comprising 11 amino acid residues, an antibody recognizing the conformational epitope of ProGRP is not induced.

Miyake et al. noted that ProGRP is more stable in the blood than GRP, and that an amino acid sequence consisting of amino acids 31-98, which is a common portion in the three species of ProGRP, does not show homology with the amino acid sequences of other proteins, and established a highly sensitive RIA method which does not need any precipitation and extraction processes, using an anti-serum of high titer obtained by using a recombinant peptide comprising the same amino acid sequence (hereinafter, referred to as ProGRP (31-98)) as an antigen (Non-Patent Document 1). In this method, it was shown that ProGRP served as an excellent tumor marker, in the same manner as GRP does.

However, although this method is advantageous in not needing extraction processes, measurement requires 4 days, and the sensitivity is only 10 pM (77.3 pg of antigen/mL), which is insufficient. Therefore, it is impossible to measure the ProGRP level in the serum of a normal person, and this method has not yet been developed to be clinically applied.

Furthermore, since the RIA methods of Holst et al. and Miyake et al. as described above are inhibition methods, measurement would be possible if only a portion of a fragment of ProGRP has antigenicity. But, the sensitivity is lower than that of sandwich methods, and clinical application of any ProGRP measuring method requiring high sensitivity is difficult. Thus, in order to clinically perform detection of ProGRP, it is essential to increase the sensitivity, and particularly, an antibody which can be used in sandwich methods is needed.

Yamaguchi, Aoyagi et al. developed, for the purpose of clinically applying ProGRP as a tumor marker for small-cell lung carcinoma, a convenient and highly sensitive reagent for measuring ProGRP using a sandwich method, which reagent is based on the principles of enzyme-linked immunosorbent assay (ELISA) (Patent Document 1). This assay gives results in about 2 hours, and shows high sensitivity (2 pg/mL). Thus, the assay is at present widely used in clinical applications, and it is obvious that this assay shows higher sensitivity and specificity compared to the assay using NSE with respect to small-cell lung carcinoma.

It was also found that by using this assay, the serum ProGRP values increased in neuroendocrine tumors (thyroid medullary carcinoma, etc.), and cancers exhibiting characteristics of neuroendocrine tumor (esophageal small cell carcinoma, pancreatic small cell carcinoma, prostate small cell carcinoma, etc.) as well as in small-cell lung carcinoma. Thus, it is believed that the ProGRP assay can be applied to early discovery or to the monitoring of treatment of patients with these tumors thereof.

However, although the stability of ProGRP in blood is higher than that of GRP, more fluctuation in the measured values is observed as compared to other common tumor markers. For this reason, there is a restriction in the method of using ProGRP as the object of detection, that the test sample for measurement must be frozen immediately after blood collection and stored until the time of measurement (Non-Patent Document 4).

[Patent Document 1] Japanese Patent No. 3210994
[Patent Document 2] Japanese Patent Application Laid-open No. 6-98794
[Non-Patent Document 1] Cancer Research, Vol. 54, pp. 2136-2140 (1994)
[Non-Patent Document 2] Spindel et al., Mol. Endocrinol., Vol. 1, pp. 224-232 (1987)
[Non-Patent Document 3] Holst, J. Clin. Oncol., Vol. 7, pp. 1831-1838 (1989)
[Non-Patent Document 4] Rinsho Kensa, Vol. 39, pp. 981-986 (1995)

DISCLOSURE OF THE INVENTION

Problems to be Solved by the Invention

The present invention is to provide a novel method for determining ProGRP, which is free from the problems observed in the conventional methods, such as fluctuation in the measured values and operational constraints involving storage of frozen test samples, although ProGRP is an object of measurement.

Means for Solving the Problems

The present invention is based on a discovery that the digest of ProGRP in the blood test sample is stably maintained, and solves the problems described above by using an epitope which is present on such stable digest, as an object of measurement. Specifically, the invention provides the following:

(1) A method for determining a gastrin-releasing peptide precursor and/or a digest thereof, using two or more different antibodies which recognize a peptide comprising a partial amino acid sequence consisting of amino acids 40 to 75 of the amino acid sequence shown in SEQ ID NO:1;

(2) A method for determining a gastrin-releasing peptide precursor and/or a digest thereof, using two or more different antibodies which recognize a peptide comprising a partial amino acid sequence consisting of amino acids 40 to 79 of the amino acid sequence shown in SEQ ID NO:1;

(3) The method according to (1) or (2), which is a sandwich immunoassay method;

(4) An antibody which binds to a peptide having a partial sequence consisting of amino acids 40 to 60 of the amino acid sequence shown in SEQ ID NO:1, and does not bind to a peptide comprising a contiguous sequence of any 8 amino acids of the amino acid sequence shown in SEQ ID NO:1;

(5) An antibody which binds to a peptide comprising a partial sequence consisting of amino acids 40 to 60 of the amino acid sequence shown in SEQ ID NO:1, and does not bind to a peptide comprising a partial amino acid sequence consisting of amino acids 31 to 53;

(6) The antibody according to (4) or (5), which is produced by hybridoma 3D6-2 deposited under Accession No. FERM BP-08669 with the International Patent Organism Depositary at the National Institute of Advanced Industrial Science And Techonolgy (AIST Tsukuba Central 6, 1-1, Higashi 1-Chome Tsukuba-shi, Ibaraki-ken 305-8566 Japan) on Mar. 23, 2004.

(7) Hybridoma 3D6-2 deposited under Accession No. FERM BP-08669.

(8) The method according to (1) or (2), wherein at least one of the two or more different antibodies is the antibody according to any one of (4) to (6).

(9) The method according to (1) or (2), wherein at least one of the two or more different antibodies is the antibody according to any one of (4) to (6), and the other is an antibody recognizing a peptide comprising a partial sequence of amino acids 71 to 75 of the amino acid sequence shown in SEQ ID NO:1.

(10) A kit for measuring a gastrin-releasing peptide precursor or a digest thereof, the kit comprising the antibody according to any one of (4) to (6).

(11) The kit according to (10), which is a kit for diagnosing cancer.

Effects of the Invention

The method of the present invention provides effects such that a sensitivity equivalent to that of conventional measurement methods can be obtained, as well as that it is hardly affected in handling of the test sample after collection and highly reproducible measured values can be obtained, and the like, by taking a newly identified epitope on the digest of ProGRP which is stably maintained even in a test sample, as an object of measurement.

BEST MODE FOR CARRYING OUT THE INVENTION

The present invention is directed to using an epitope present on a digest of ProGRP (ProGRP-Cdel) in a test sample, which has higher storage stability in the blood compared to ProGRP or ProGRP-Cfrag, as an object of an immunological measuring method.

This ProGRP-Cdel is a peptide having a shorter chain length, resulting from deletion of several amino acid residues from the C-terminal of ProGRP-Cfrag which is the object of measurement in conventional methods, and is a peptide containing an epitope residing within the amino acids 40 to 75 of ProGRP. It is suspected that ProGRP-Cdel is generated when the C-terminal side of any residues among amino acid residues 75 to 83 of ProGRP-Cfrag has been cleaved by a protease present in the blood.

With regard to this ProGRP-Cdel, its structure was examined using a mass analysis apparatus, and it was confirmed that the $79^{th}$ Lys was cleaved on the C-terminal side. Thus, ProGRP-Cdel is also a peptide containing an epitope which resides within amino acid residues 40 to 79 of the amino acid sequence shown in SEQ ID NO:1, and thus an antibody recognizing such epitope can also be used in the present invention.

The difference in structure between ProGRP-Cdel and ProGRP-Cfrag is merely the presence or absence of approximately 20 amino acid residues on the C-terminal side, but the significance of these fragments as an object protein for immunologically determining ProGRP or a digest thereof is greatly different. In conventional methods, an antibody which recognizes the aforementioned part of about 20 residues on the C-terminal side is used. Therefore, this antibody now cannot recognize and capture ProGRP-Cdel which has lost that part. The cleavage process of this part on the C-terminal side is affected by the test sample itself, or by the storage condition or storage period after collection of the test sample, and this is suspected to the cause for that detection signals are affected by the storage condition of a test sample or the storage period in conventional methods.

Meanwhile, the present invention is to use an antibody which recognizes the epitope residing in ProGRP-Cdel; thus, even if ProGRP or ProGRP-Cfrag is present in the test sample, and even if cleavage of that part occurs, the antibody can stably recognize ProGRP or a digest thereof. Accordingly, the detection signal is less affected by the storage condition of the test sample or the storage period, and highly reproducible measurement is made possible.

The present invention is a method for detecting ProGRP or a digest thereof according to a sandwich immunoassay method, using different antibodies which are selected from antibodies that can recognize the epitope present on the peptide having a sequence of amino acids 40 to 75 of ProGRP (ProGRP (40-75)) and which independently recognize two or more different epitopes that are present in ProGRP (40-75), so as to employ an epitope on ProGRP-Cdel as the object of determination. Furthermore, the present invention is a method for detecting ProGRP or a digest thereof according to a sandwich immunoassay method, using different antibodies which are selected from antibodies that can recognize the epitope present on the peptide having a sequence of amino acids 40 to 79 of ProGRP (ProGRP (40-79)) and which independently recognize two or more different epitopes that are present in ProGRP (40-79).

In particular, according to the present invention, it is preferable to use a sandwich immunoassay method which does not involve the antibody for recognizing the epitope on the partial sequence on the C-terminal that has been eliminated by cleavage from ProGRP-Cfrag, but involves only the antibody for recognizing the epitope on ProGRP-Cdel.

The fundamental operation of sandwich ELISA may be conducted according to a method described in "Ultrasensitive Immunoassay" (Eiji ISHIKAWA, Japan Scientific Societies Press (1993)) or other various manuals for experimental techniques. It is conceived that implementation of the present invention does not require any special operation, but the present invention can be carried out by the following process.

Specifically, ProGRP or a digest thereof can be detected according to a method for determination comprising the steps of: (1) reacting a first antibody which binds to ProGRP (40-75) and/or ProGRP (40-79), with ProGRP or a digest thereof in a test sample; (2) reacting the ProGRP or a digest thereof which has been captured by the antibody, with a second antibody which is different from the antibody of the step (1)

but binds to proGRP (40-75) and/or ProGRP (40-79); and (3) detecting the immune complex generated in the step (2).

With regard to the antibody which binds to ProGRP or a digest thereof, it is preferable to select for use only an antibody which binds to ProGRP (40-75) and/or ProGRP (40-79), but other antibodies except for such antibodies may be contained in the determination system, within the range that measured values can be highly reproduced.

A particularly preferred combination of antibodies in the present invention is a combination of monoclonal antibody GRP-3D6-2 which recognizes the sequence of amino acids 40 to 60 of ProGRP, and monoclonal antibody GRP-2B10 which recognizes the sequence of amino acids 71 to 75 of ProGRP. The monoclonal antibody GRP-3D6-2 recognizes the sequence of amino acids 40 to 60 of the amino acid sequence of ProGRP, but does not recognize at the same time a peptide comprising a contiguous sequence of any 8 amino acids in the same amino acid sequence. In view of this, it is conceived that the monoclonal antibody GRP-3D6-2 is an antibody recognizing the conformational epitope having a sequence of amino acids 40 to 60 of the amino acid sequence of ProGRP. The monoclonal antibody GRP-2B10 is assumed to recognize the sequence epitope which is composed of the amino acid residues 71 to 75.

The assay of the present invention which uses two types of monoclonal antibodies as described above can detect 4.5 pg of ProGRP/ml. This value is almost equal to the sensitivities of conventional methods using monoclonal antibodies and polyclonal antibodies for determining proGRP (31-98), and indicates a sensitivity which can be sufficiently used in the determination of ProGRP concentration in the blood from a normal person.

The antibodies used in the present invention can be obtained by immunizing laboratory animals such as mice, rats, guinea pigs, rabbits, chickens, goats, sheep and cattle. For the antigen used in immunization, although it is preferable to use ProGRP (40-75) and/or ProGRP (40-79), the peptide of ProGRP (31-98) can also be used, and desired antibodies can be obtained by selecting with the use of ProGRP (40-75) and/or ProGRP (40-79) after immunization.

The method of immunizing an animal will be described by taking an example of a mouse. The peptide of ProGRP (31-98) or the like is mixed with an adjuvant such as Freund's complete adjuvant or TiterMax Gold (CytRx Corp.), at a ratio of 1:1, and is repeatedly passed through a joint comprising two syringes joined at a cross-flow joint or ultrasonicated to form an emulsion. The antigen-containing emulsion thus prepared is injected subcutaneously, intradermally, intramuscularly or intraperitoneally, or at multiple sites. After completion of the first immunization, a booster immunization can be conducted in the same manner at an interval of 1 to 4 weeks. Thereafter, immunization is continued in the same manner, until the antibody titer of the antibody directed to ProGRP (31-98) in the blood increases.

The antibody titer can be determined as follows. ProGRP (31-98) is dissolved in PBS to a concentration of 1 μg/ml, and 50 μL of the solution is added to each well of a 96-well microtiter plate, and this peptide is adsorbed overnight at 4° C. Each well is used for assay after being washed with PBS containing 0.05% Tween 20 (PBS-T). Prior to the assay, blocking may be performed with PBS containing 1% BSA or the like. Blood is collected from the orbital venous plexus, the caudal vein, the caudal artery or the like, diluted to 30-folds with PBS-T, and then centrifuged. The obtained supernatant is prepared into a series of dilutions with PBS-T, and 50 μL each is added to each well of a microtiter plate coated with ProGRP (31-98). Each well is incubated at room temperature for 30 minutes, and then the plate is washed with PBS-T, 50 μL of a horseradish peroxidase (HRP)-labeled anti-mouse IgG solution which has been appropriately diluted with PBS-T is added to each well. The each well is further incubated at room temperature for 30 minutes, subsequently a substrate solution containing hydrogen peroxide and orthophenylenediamine is added to each well, and then is incubated for 30 minutes. 50 μL of 2 N $H_2SO_4$ is added to stop the reaction, and the absorbance of each well is measured.

After confirming that the antibody titer against ProGRP has sufficiently increased in the immunized mouse, the spleen is extracted, and the spleen cells are isolated. These cells are fused with separately cultured mouse myeloma cells (for example, SP2/0-Ag14, etc.), using polyethylene glycol or the like. The successfully fused cells are selectively cultured in HAT (hypoxanthine/aminopterin/thymidine) medium. Culturing is continued while exchanging half the amount of the medium every few days for about 7 to 14 days, and then the antibody titer of the culture supernatant is measured. The positive well cells are cloned by the limiting dilution method to obtain hybridomas producing the desired antibody. As the hybridoma obtained by the above-described method, 3D6-2 (Accession No. FERM BP-8669) and ProGRP-2B10 (Accession No. FERM BP-4110) may be mentioned.

By analyzing the epitope of the antibody obtained by the above-described method, an antibody which recognizes and binds to the epitope present on ProGRP (40-75) and/or ProGRP (40-79) can be acquired. Epitope analysis can be carried out by examining the reaction of the antibody directed against ProGRP (40-75) and/or ProGRP (40-79). It is determined by coating a microtiter plate with ProGRP (31-98) or ProGRP (40-75) and/or ProGRP (40-79) that has been recombinantly expressed, or with proGRP (40-75) and/or ProGRP (40-79) that has been chemically synthesized by the Fmoc method or Boc method, and examining the reaction concerning each peptide by the immunoassay method described above. Furthermore, the epitope present on a peptide comprising about 8 to 12 consecutive amino acids of ProGRP can be determined using a peptide synthesized by the multipin peptide synthesis method.

According to the present invention, it is also possible to immobilize the antibody into the solid-phase, or to label the antibody. The respective processes may be performed according to the methods described in various manuals for experimental techniques, and no special operation would be particularly necessary in implementing the present invention.

In addition to the method described above, the present invention also provides a kit for determining ProGRP or a digest thereof in a test sample, and particularly a kit of diagnostic agent for diagnosing small-cell lung carcinoma or for monitoring of chemotherapy by determining ProGRP or a digest thereof. Such a kit comprises at least two antibodies which recognize the epitope present on the above-described ProGRP (40-75) and/or ProGRP (40-79), and may also comprise any of a reaction solution, a diluent of a second antibody, a ProGRP standard substance, instructions and other constituents. Preferred examples of the antibody contained in the kit include an antibody which recognizes the epitope present on ProGRP (40-75) and/or ProGRP (40-79), but does not recognize a peptide comprising any 8 consecutive amino acid residues present on the same peptide, and an antibody which recognizes the sequence of amino acids 71 to 75 of ProGRP, and representative examples include monoclonal antibody GRP-3D6-2 and monoclonal antibody GRP-2B10.

Hereinafter, the present invention will be explained by way of Examples.

EXAMPLE 1

Preparation of Hybridoma

A recombinant was prepared by the method described in Example 1 of Japanese Patent No. 3210994, and a peptide having the amino acid sequence shown in SEQ ID NO:4, which was expressed by *Escherichia coli*, was purified. In Example 1 of Japanese Patent No. 3210994, this recombinant protein was described to be GRP (31-98), but it is actually the (31-98) part of GRP precursor (ProGRP), and thus will be described herein as ProGRP (31-98). Subsequently, the hybridoma producing the monoclonal antibody of the present invention was obtained by the method described in Example 6 of the Japanese Patent No. 3210994.

The obtained hybridoma 3D6-2 (FERM BP-8669) is deposited with the International Patent Organism Depositary at the National Institute of Advanced Industrial Science And Technology (AIST Tsukuba Central 6, 1-1, Higashi 1-Chome Tsukuba-shi, Ibaraki-ken 305-8566 Japan) on Mar. 23, 2004, and proGRP-2B10 (FERM BP-4100) and proGRP-3G2 (FERM BP-4109) are deposited with the Fermentation Research Institute (currently, the International Patent Organism Depositary at the National Institute of Advanced Industrial Science and Technology (AIST Tsukuba Central 6, 1-1, Higashi 1-Chome Tsukuba-shi, Ibaraki-ken 305-8566 Japan)) on Dec. 9, 1992.

The obtained hybridoma was transplanted into the peritoneal cavity of a mouse which had been treated with pristane or the like, the ascites was recovered, and the respective monoclonal antibodies were purified from the ascites using a Protein A-bound Sepharose column. The monoclonal antibody obtained from hybridoma 3D6-2 (FERM BP-8669) was designated as GRP-3D6-2.

EXAMPLE 2

Epitope Analysis of Monoclonal Antibody (1) Synthesis of Peptide and Determination of Epitope The nucleic acid sequence and amino acid sequence of ProGRP (31-98) are shown in SEQ ID NO:3. According to this amino acid sequence, a partial peptide of ProGRP (31-98) was synthesized by the Fmoc method. Pep1 is a peptide having the sequence of amino acids 31 to 52 of ProGRP, Pep70 is a peptide having the sequence of amino acids 40 to 60, Pep3 is a peptide having the sequence of amino acids 54 to 78, Epi2 is a peptide having the sequence of amino acids 70 to 90, and Pep5 is a peptide having the sequence of amino acids 82 to 96. The synthesized peptides were purified by reverse phase chromatography, or by a combination of reverse phase chromatography and gel filtration. The purity after purification was 80% or higher.

Each peptide was diluted in PBS to a concentration of 1 µg/mL, and 100 µL of each peptide solution was added to each well of a 96-well microtiter plate, and each well was incubated overnight at 4° C. Each well was washed twice with PBS, and PBS containing 1% BSA was added to each well. The plate was incubated at room temperature for 2 hours, and PBS containing 1% BSA was removed by aspiration. The monoclonal antibody GRP-3D6-2 diluted to a concentration of 1 µg/mL was added to each well at 100 µL volume each, and the each well was incubated at room temperature for 60 minutes. Subsequently, the plate was washed 5 times with PBS containing 0.05% Tween 20 (PBS-T), 100 µL of a horseradish peroxidase (HRP)-labeled anti-mouse IgG antibody solution was then added to each well, and the each well was incubated at room temperature for 30 minutes. The each well was washed 5 times with PBS-T, and then 100 µL of a substrate solution (0.1 M citrate phosphate buffer solution containing 2 mg/mL of ortho-phenylenediamine and 0.9 µL/mL of a 30% aqueous hydrogen peroxide solution, pH 5.0) was added to each well. The each well was incubated at room temperature for 30 minutes, and then 100 µL each of 2 N sulfuric acid was added to each well to stop the reaction. Immediately, the absorbance was measured at 492 nm, and the results are shown in Table 1.

TABLE 1

| Peptide | a.a. No | OD492/630 |
| --- | --- | --- |
| Pep 1 | 31-52 | 0.003 |
| Pep 70 | 40-60 | 0.822 |
| Pep 3 | 54-78 | 0.003 |
| Epi 2 | 70-90 | 0.004 |
| Pep 5 | 82-96 | 0.002 |
| ProGRP | 31-98 | 2.236 |

The monoclonal antibody GRP-3D6-2 reacted to recombinant ProGRP (31-98), which was a positive control, and to Pep70, which was the amino acid sequence of amino acids 40 to 60 of ProGRP. In view of this, it was found that GRP-3D6-2 recognizes the amino acid sequence of amino acids 40 to 60 of ProGRP. Furthermore, in a similar manner, it was found that GRP-2B10 reacts to the peptides of Pep3 and Epi2, and GRP-3G2 reacts to the peptides of Epi2 and Pep5.

(2) Synthesis of Multipin Peptide and Determination of Epitope

Based on the amino acid sequence of ProGRP (31-98), 61 peptides comprising 8 consecutive amino acids with 1 amino acid overlapped in each peptide, were synthesized by the multipin peptide synthesis method. Each peptide was conjugated with biotin at the terminals, and the synthesis was performed by Wako Pure Chemical Industries, Ltd. (Japan, Osaka) upon request.

Each of the biotinylated peptides which were synthesized by the multipin peptide method was dissolved in dimethylformamide, and the solution was diluted with PBS to a concentration of 1 µg/mL. 100 µL of this diluted solution of biotinylated peptide was added to the avidin coated each well of a 96-well microtiter plate, and each well was incubated overnight at 4° C. Each well was washed with PBS containing 0.05% Tween 20 (PBS-T), and then 100 µL of each solution of monoclonal antibody GRP-3D6-2, GRP-3G2 and GRP-2B10, respectively diluted to 1 µg/mL, were added to each well. After incubation at room temperature for 30 minutes, the each well was washed 5 times with PBS-T, 100 µL of a horseradish peroxidase (HRP)-labeled anti-mouse IgG antibody solution was added to each well. Each well was further incubated for 30 minutes at room temperature, and then the each well was washed 5 times with PBS-T. 100 µL of a substrate solution (0.1 M citrate phosphate buffer solution containing 2 mg/mL of ortho-phenylenediamine and 0.9 µL/mL of a 30% aqueous hydrogen peroxide solution, pH 5.0) was added to each well. The each well was incubated at room temperature for 30 minutes, and then 100 µL each of 2 N sulfuric acid was added to each well to stop the reaction. Immediately, the absorbance was measured at 492 nm. The respective reactions of monoclonal antibodies GRP-3D6-2, GRP-3G2 and GRP-2B10 against the respective peptides within ProGRP (31-98) are shown in FIGS. 1(A), 1(B) and 1(C).

Figure 1:
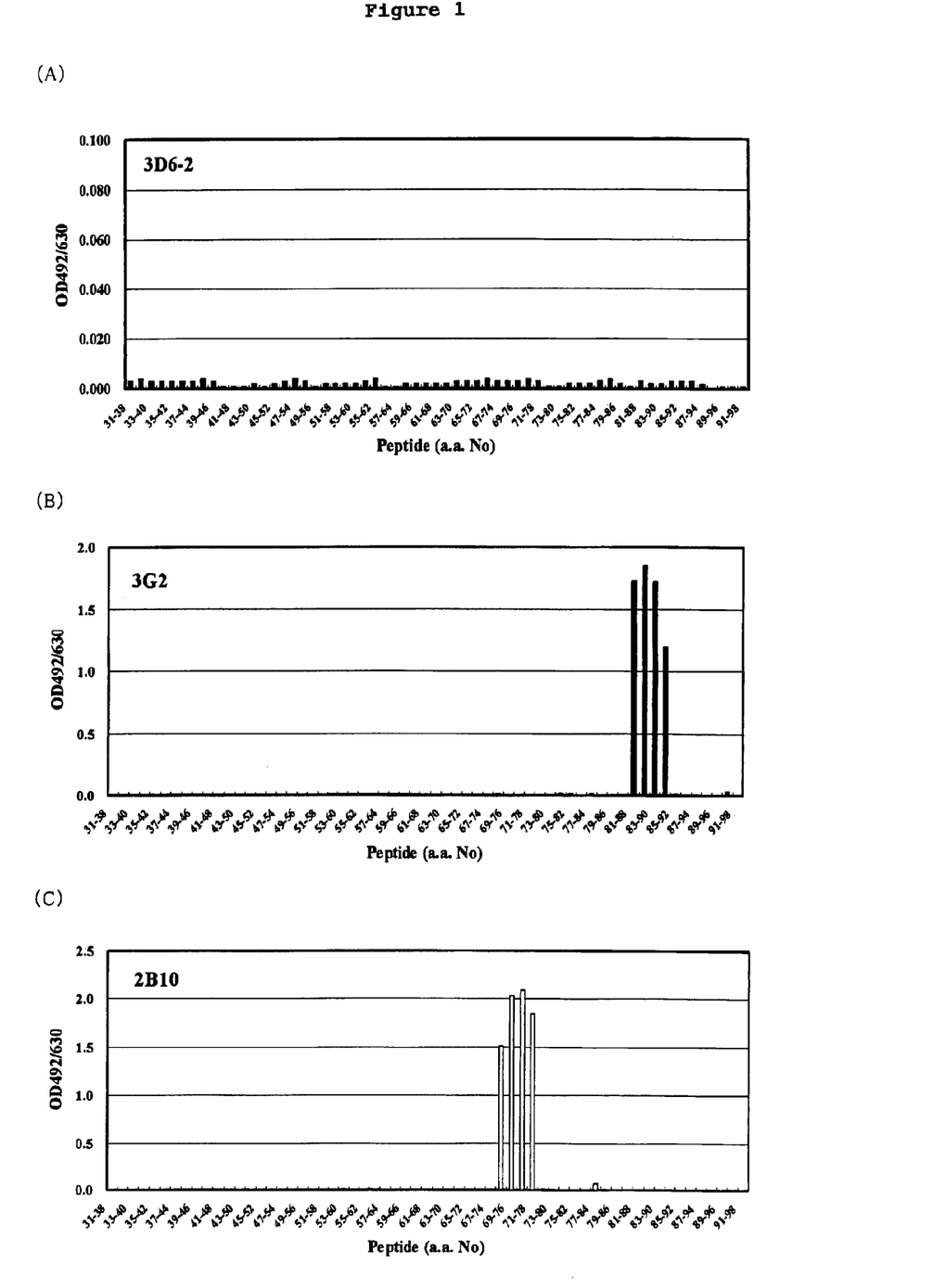
FIG. 1 shows the reactivity of a monoclonal antibody directed to a peptide comprising a contiguous sequence of 8 amino acids, which was synthesized by multipin peptide synthesis method. The horizontal axis indicates the contiguous 8 sequence of amino acid of ProGRP (31-98), while the vertical axis indicates absorbance. (A), (B) and (C) indicate the reactivity of GRP-3D6-2, GRP-3G2 and GRP-2B10, respectively.

As shown in FIG. 1(A), the monoclonal antibody GRP-3D6-2 did not bind to the peptides comprising 8 consecutive amino acids within ProGRP (31-98). This is believed to be because GPR-3D6-2 does not recognize peptides comprising 8 consecutive amino acids of ProGRP, and recognizes a conformational epitope prepared from a peptide comprising longer than 8 amino acids. On the other hand, the monoclonal antibody GRP-3G2 was bound to four peptides comprising 8 consecutive amino acids, such as amino acids 81 to 88, 82 to 89, 83 to 90, and 84 to 91. It is conceived that the monoclonal antibody GRP-3G2 recognizes the peptide of amino acids 84 to 88, which is a sequence present in these four peptides (FIG. 1(B)). Furthermore, the monoclonal antibody GRP-2B10 bound to four peptides comprising 8 consecutive amino acids, such as amino acids 68 to 75, 69 to 76, 70 to 77, and 71 to 78. For this reason, it is conceived that the monoclonal antibody GRP-2B10 recognizes the peptide of amino acids 71 to 75, which is a sequence present in these four peptides (FIG. 1(C)).

In view of the results of epitope analysis using these peptides, the epitope recognized by the monoclonal antibody GRP-3G2 or the monoclonal antibody GRP-2B10 is formed from 5 consecutive amino acid residues.

Furthermore, the monoclonal antibody GRP-3D6-2 recognizes a peptide of at least the part comprising amino acids 40 to 60 of ProGRP (31-98), and does not bind to a peptide comprising 8 consecutive amino acids within the amino acid sequence of ProGRP (31-98). In other words, it is conceived that GPR-3D6-2 recognizes a conformational epitope which is formed in the amino acid sequence of at least the amino acids 40 to 60 of ProGRP (31-98), but is not formed in peptides each comprising 8 consecutive amino acids.

A summary of the relationships of the epitopes recognized by the monoclonal antibodies as described above is shown in Table 2.

TABLE 2

| Monoclonal antibody | Epitope(Amino acids No. of ProGRP) |
|---|---|
| GRP-3G2 | 84-88 |
| GRP-2B10 | 71-75 |
| GRP-3D6-2 | 40-60 |

EXAMPLE 3

Examination of Storage Stability of Test Sample Achieved by Combination of Monoclonal Antibodies To each well of a 96-well microplate, one or two monoclonal antibodies (in the case of two species, a mixture of equal amounts) were added at 100 µL volume at a concentration of 4 µg/mL, and immobilized by incubation overnight at 4° C. The microplate was washed twice with 10 mM phosphate buffer solution containing 0.15 M NaCl (pH 7.3), and then blocked by adding 350 µL of a blocking solution (10 mM phosphate buffer solution containing 0.5% casein sodium, pH 7.1) and allowing to stand for 2 hours. After removing the blocking solution, 100 µL of the reaction solution and 50 µL of the test sample to be determined were added to each well, and incubated for 1 hour at 37° C. After washing 5 times with a washing solution (10 mM phosphate buffer solution containing 0.05% Tween 20, pH 7.3), 100 µL of a solution of one or two types of HRP-labeled monoclonal antibodies (in the case of two species, a mixture of equal amounts) was added and was incubated for 30 minutes at room temperature. After washing 5 times with the washing solution, 100 µL of a substrate solution (0.1 M citrate phosphate buffer solution containing 2 mg/mL of ortho-phenylenediamine and 0.9 µL/mL of a 30% aqueous hydrogen peroxide solution, pH 5.0) was added. The each well was incubated for 30 minutes, and then 100 µL each of 2 N sulfuric acid was added to stop the enzymatic reaction. Immediately, the absorbance was measured at 492 nm (reference wavelength: 630 nm) with a microplate reader.

Using this method of measurement, three test samples were respectively divided into a sample stored frozen at −20° C. and a sample stored at room temperature for 17 hours, for measurement. The ProGRP value of the sample stored frozen was set as a control (100%), and the measured values of the samples stored at room temperature for 17 hours were indicated in percentage (Table 3). When the combinations of an immobilized antibody and a labeled antibody were GRP-3G2 and GRP-2B10, GRP-3G2 and GRP-3D6-2, GRP-3G2 and GRP-2B10/GRP-3D6-2, respectively, the immunoactivities of ProGRP in the test samples stored for 17 hours were decreased on the average to 69.6%, 70.6% and 69.2%, respectively. Also, in the case of GRP-3G2/GRP-2B10 and a polyclonal antibody, which is a combination of an immobilized antibody and a labeled antibody according to conventional methods, the value decreased to 71.8%. On the other hand, in the case of using GRP-3D6-2 for the immobilized antibody and GRP-2B10 for the labeled antibody, even after storing at room temperature for 17 hours, the measured value was 89.3% on the average, and the immunoactivity of ProGRP was maintained to be about 20% higher than that of other antibody combinations (Table 3). In addition, the polyclonal antibody used was one acquired by the method described in Example 8 of Japanese Patent No. 3210994.

TABLE 3

| Sample No. | Solid phase Conjugate | GRP-3G2 GRP-2B10 | GRP-3G2 GRP-3D6-2 | GRP-3G2 GRP-2B10/ GRP-3D6-2 | GRP-3D6-2 GRP-2B10 | GRP-3G2 GRP-2B10 Polyclonal antibody |
|---|---|---|---|---|---|---|
| 729 | | 66.3 | 66.8 | 66.5 | 82.1 | 71.6 |
| 857 | | 71.6 | 73.7 | 70.0 | 92.5 | 72.9 |
| 815 | | 70.7 | 71.1 | 71.0 | 93.3 | 70.9 |
| | Mean recovery % | 69.6 | 70.6 | 69.2 | 89.3 | 71.8 |

EXAMPLE 4

Method of Determination Using Antibody Binding to Pro-GRP (40-75)

Figure 2:
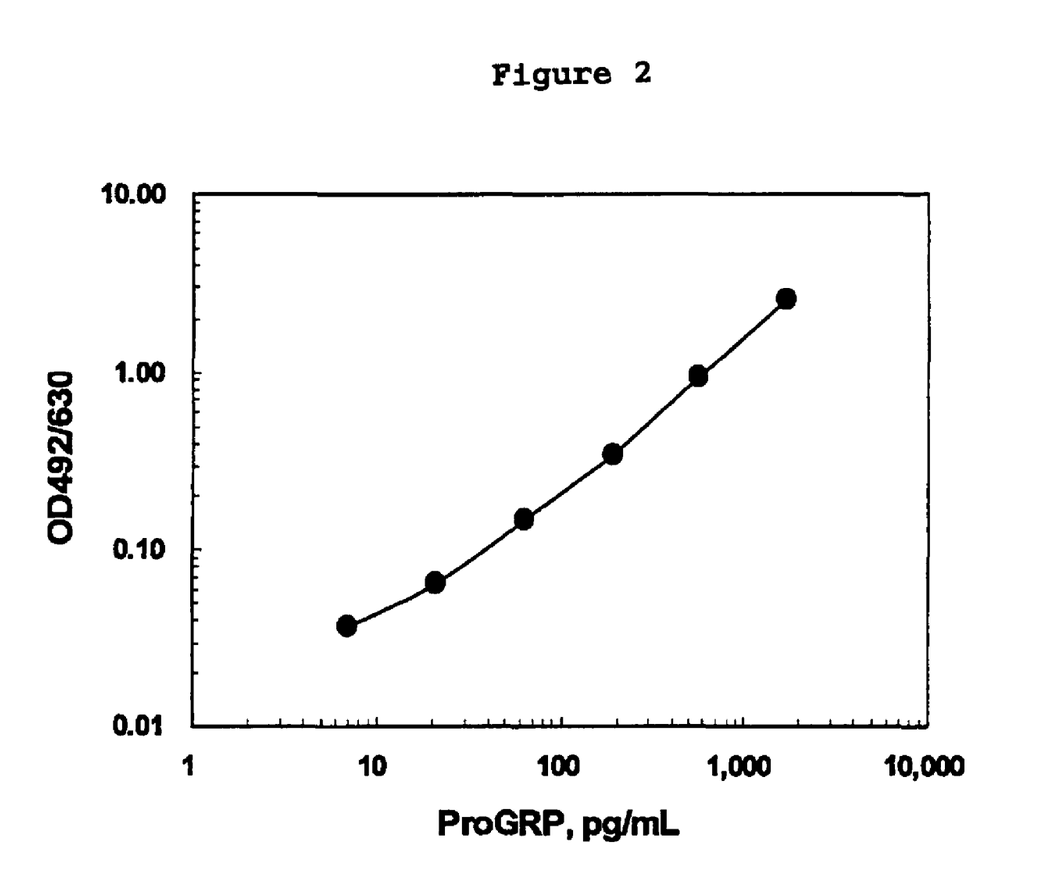
FIG. 2 shows a standard curve for the measurement method, obtained by using GRP-3D6-2 and GRP-2B10 which are antibodies that bind to a partial peptide consisting of amino acids 40 to 75. The horizontal axis indicates the concentration of ProGRP, while the vertical axis indicates absorbance.

To each well of a 96-well microplate, GRP-3D6-2 was added at 200 μL volume at a concentration of 4 μg/mL, and the microplate was incubated overnight at 4° C. The microplate was washed twice with 10 mM phosphate buffer solution containing 0.15 M NaCl (pH 7.3), and then blocked by adding 350 μL of a blocking solution (10 mM phosphate buffer solution containing 0.5% casein sodium, pH 7.1) and allowing to stand for 2 hours. After removing the blocking solution, 100 μL of the reaction solution and 100 μL of the test sample to be determined were added to each well, and incubated for 1 hour at 37° C. After washing 5 times with a washing solution (10 mM phosphate buffer solution containing 0.05% Tween 20, pH 7.3), 200 μL of a HRP-labeled GRP-2B10 solution was added and incubated for 30 minutes at room temperature. After washing 5 times with the washing solution, 200 μL of a substrate solution (0.1 M citrate phosphate buffer solution containing 2 mg/mL of ortho-phenylenediamine and 0.9 μL/mL of a 30% aqueous hydrogen peroxide solution, pH 5.0) was added. The each well was incubated for 30 minutes, and then 50 μL of 5 N sulfuric acid was added to stop the enzymatic reaction. Immediately, the absorbance was measured at 492 nm (reference wavelength: 630 nm) with a microplate reader. The standard curve is shown in FIG. 2.

In view of this standard curve, it is believed that about 4.5 pg/mL of ProGRP can be detected. The sensitivity in this assay is sufficient for detecting the amount of ProGRP in the sample from a healthy person.

TEST EXAMPLE 1

Using a conventional method and the assay method of Example 4 of the present invention, five test samples were stored for 1, 3 and 7 days at 4° C., and then the immunoreactivity of ProGRP in the test samples were measured and compared with the measured values of the same samples before storage. The conventional method was carried out in the following manner. To each well of a 96-well microplate, 100 μL of GRP-3G2 and GRP-2B10 (a mixture of equal amounts) at a concentration of 10 μg/mL was added, and immobilized by incubation overnight at 4° C. The microplate was washed twice with 10 mM phosphate buffer solution containing 0.15 M NaCl (pH 7.3), and then blocked by adding 350 μL of a blocking solution (10 mM phosphate buffer solution containing 0.5% casein sodium, pH 7.1) and allowing to stand for 2 hours. After removing the blocking solution, 100 μL of the reaction solution and 50 μL of the test sample to be determined were added to each well, and incubated for 1 hour at 37° C. After washing 5 times with a washing solution (10 mM phosphate buffer solution containing 0.05% Tween 20, pH 7.3), 100 μL of a HRP-labeled polyclonal antibody solution was added and incubated for 30 minutes at room temperature. After washing 5 times with the washing solution, 100 μL of a substrate solution (0.1 M citrate phosphate buffer solution containing 2 mg/mL of ortho-phenylenediamine and 0.9 μL/mL of a 30% aqueous hydrogen peroxide solution, pH 5.0) was added, the each well was incubated for 30 minutes, and then 100 μL of 2 N sulfuric acid was added to stop the enzymatic reaction. Immediately, the absorbance was measured at 492 nm (reference wavelength: 630 nm) with a microplate reader.

The value of ProGRP measured before storing at 4° C. was set as 100%, and the values measured after the respective storage periods were indicated in percentage. The results are shown in Table 4.

In the case of the conventional method, the measured values for ProGRP in the test samples were 94.5% on the average after a storage period of 1 day at 4° C., 85.8% on the average after a storage period of 3 days, and 67.8% on the average after a storage period of 7 days, and thus the activity tended to decrease by about 4.93% on the average per day. On the other hand, in the assay method of the present invention, the measured values for ProGRP in the test samples were 96.9% on the average after a storage period of 1 day at 4° C., 94.3% on the average after a storage period of 3 days, and 86.9% on the average after a storage period of 7 days, and thus the activity tended to decrease by about 2.29% on the average per day. That is, the assay method of the present invention showed a storage stability which was 2.15 times higher than that of the conventional method, and particularly after a storage period of 7 days, the immunoreactivity of ProGRP was maintained to be about 19% higher than that of the conventional method.

TABLE 4

| Solid phase Conjugate | Conventional method GRP-2B10&GRP-3G2 /Polyclonal antibody | | | Present invention GRP-3D6-2 /GRP-2B10 | | |
|---|---|---|---|---|---|---|
| storage period | 1 day | 3 days | 7 days | 1 day | 3 days | 7 days |
| Sample No. 115 | 92.3 | 84.0 | 63.4 | 97.8 | 94.2 | 85.7 |
| 822 | 92.9 | 85.1 | 65.6 | 98.6 | 95.6 | 91.3 |
| 215 | 95.8 | 78.8 | 66.0 | 100.0 | 95.5 | 91.0 |
| 1029 | 93.3 | 92.0 | 66.7 | 86.6 | 86.7 | 76.5 |
| 857 | 98.4 | 89.0 | 77.4 | 101.5 | 99.6 | 89.8 |
| Average, % | 94.5 | 85.8 | 67.8 | 96.9 | 94.3 | 86.9 |

TEST EXAMPLE 2

Analysis of the epitopes which are respectively recognized by the monoclonal antibodies GRP-3G2, GRP-2B10 and GRP-3D6-2 that can be used in the present invention, was conducted.

A peptide having a sequence of amino acids 31 to 53 of ProGRP was synthesized by the Fmoc method. The synthesized peptide was purified by reverse phase chromatography, or by a combination of reverse phase chromatography and gel filtration. The respective peptides, including the peptide used in Example 2, were dissolved in 0.1% TFA, and were diluted with PBS to a concentration of 10 μg/mL. To each well of a 96-well microtiter plate, 100 μL of each of the dilutions was added to each well of a 96-well ELISA plate, and was allowed for adsorption overnight at 4° C. Each well was washed twice with PBS, PBS containing 1% BSA was added to each well, the plate was incubated at room temperature for 2 hours, and then the buffer solution was removed by aspiration. 100 μL of monoclonal antibodies GRP-3G2, GRP-2B10 and GRP-3D6-2, respectively diluted to a concentration of 5 μg/mL, were added to each well. Each well was incubated at room temperature for 85 minutes, and then the plate was washed 5 times with PBS containing 0.05% Tween 20 (PBS-T). 100 μL of a horseradish peroxidase (HRP)-labeled anti-mouse IgG solution appropriately diluted with PBS-T was added to each well, and the each well was further incubated at room temperature for 30 minutes. After washing the plate 5 times with PBS-T, 100 μL of a substrate solution (0.1 M citrate phosphate buffer solution containing 2 mg/mL of ortho-phenylenediamine and 0.9 μL/mL of a 30% aqueous hydrogen peroxide solution, pH 5.0) was added to each well, the each well was incubated at room temperature for 20 minutes, and then 100 μL each of 2 N sulfuric acid was added to stop the reaction. Immediately, the absorbance was measured at 492 nm. The results are shown in Table 5.

TABLE 5

| Peptide | GRP-3D6-2 | GRP-3G2 | GRP-2B10 |
|---------|-----------|---------|----------|
| 31-53 | 0.003 | 0.006 | 0.006 |
| 40-60 | 1.477 | 0.005 | 0.004 |
| 54-78 | 0.005 | 0.027 | 2.052 |
| 70-90 | 0.004 | 1.953 | 1.830 |
| 82-96 | 0.005 | 1.425 | 0.060 |
| 31-98 | 2.063 | 2.146 | 2.145 |

In view of Table 5, the epitopes which are reactive to GRP-3G2, GRP-2B10 and GRP-3D6-2 show nearly the same results as the results shown in Example 2, and it was confirmed that since GRP-3D6-2 does not completely bound to the sequence of amino acids 31 to 53, it does not also bound to the peptide of amino acid sequences 42 to 53.

TEST EXAMPLE 3

Identification of ProGRP-Cdel was performed using a mass analysis apparatus (LC-MS/MS). A rabbit polyclonal antibody exhibiting reactivity to various peptides in the Pro-GRP (31-98) region was dissolved in PBS to a concentration of 12.7 mg/ml, and was bound to 3 ml of NHS-Sepharose (Amersham PLC.) according to the user manual.

To 1.5 ml of two human sera, 20 µg of recombinant Pro-GRP (31-98) was added and maintained at room temperature for 24 hours. Thereafter, 0.4 ml of the above-mentioned rabbit polyclonal antibody-bound Sepharose was added, and the mixture was stirred for 60 minutes at room temperature. This rabbit polyclonal antibody-bound Sepharose was washed away with a washing solution (10 mM phosphate buffer solution containing 0.05% Tween 20, pH 7.3), and 0.5 ml of 9.5 M urea solution was added, and the substance bound to the rabbit polyclonal antibody-bound Sepharose was eluted out. The eluate was recovered, and then, the maintained peptide of the ProGRP (31-98) region in this elute was examined using LC-MS/MS.

1 µl of 250 mM of Methyl-PEO$_4$—NHS ester (Pierce LLC) solution/DMSO was added to 100 µl of the eluate, and the mixture was incubated at room temperature for 1 hour. 5 µl of 1 M Tris-HCl (pH 8) was added, and the mixture was incubated at room temperature for 30 minutes to stop the reaction. Subsequently, 800 µl of acetone was added to precipitate the protein. After centrifuging, pellets were dried, and 15 µl of a modified trypsin solution from Promega Corp. (20 ng/µl/50 mM ammonium hydrogen carbonate) was added thereto to digest the protein overnight at 30° C. After digestion, 15 µl of 0.1% formic acid was added to the sample, and the sample was centrifuged for 5 minutes at 15000 rpm. 5 µl of the supernatant thus obtained was subjected to LC-MS/MS analysis {(LC part) Agilent 1100 series capillary LC system, (column) Agilent Zorbax SB-C18, 5 µm, 150×0.5 mm, (MS/MS) Bruker Daltonics HCT-plus}. Separation was performed in the presence of 0.1% formic acid, the flow rate was 15 µl/min, and the acetonitrile gradient was performed with 0-35% linear/0-120 min, 35-95% linear/120-125 min. The column eluate was introduced to the ESI part, and MS/MS data was attained. A peak list was prepared with a Data Analysis software, and analysis was performed using a MASCOT server of Matrix Science, Ltd.

Methyl-PEO$_4$—NHS has a property of modifying the N-terminal amino group and the side chain amino group of lysine in the protein molecule. Therefore, if there is any discovered peptide fragment having a labeled N-terminal amino group, this can be considered to have been in an N-terminal-free state before trypsin-digestion. Also, since digestion by trypsin does not occur at the site of lysine with labeled side chain amino group, if a side chain of lysine at the C-terminal is labeled, this protein has already been cleaved at this part before trypsin-digestion. In both human serum samples, NHQPPQPK (72-79) (SEQ ID NO: 5) was found as the fragment with labeled C-terminal lysine. Accordingly, it is conceived that a fragment cleaved from at least the C-terminal side of Lys-79 was generated by serum treatment. Furthermore, although the N-terminal side was not labeled, a fragment of SVSER (37-41) (SEQ ID NO: 6) was observed in both human serum samples. Thus, a possibility for cleavage on the C-terminal side of Ser-36 was suggested.

INDUSTRIAL APPLICABILITY

The method of the present invention selects an epitope on a digest of ProGRP which is stably stored in the test sample, as the object of measurement. Thus, the method of the present invention is equally sensitive to the conventional assay and has some advantages such that the test sample is hardly affected by handling after sampling, and that it is possible to obtain highly reproducible measured values. Thus, the method of the present invention is effective in detection of ProGRP in the blood.

The invention claimed is:

1. A method for determining a gastrin-releasing peptide precursor or a digest thereof, comprising contacting a test sample with two or more different antibodies which recognize a peptide comprising a partial amino acid sequence consisting of amino acids 40 to 75 of the amino acid sequence shown in SEQ ID NO:2, wherein at least one antibody is a monoclonal antibody which is produced by hybridoma 3D6-2 deposited under Accession No. FERM BP-08669.

2. A method for determining a gastrin-releasing peptide precursor or a digest thereof, comprising contacting a test sample with two or more different antibodies which recognize a peptide comprising a partial amino acid sequence consisting of amino acids 40 to 79 of the amino acid sequence shown in SEQ ID NO:2, wherein at least one antibody is a monoclonal antibody which is produced by hybridoma 3D6-2 deposited under Accession No. FERM BP-08669.

3. The method according to any one of claim 1 or 2, which is a sandwich immunoassay method.

4. The method according to any one of claim 1 or 2, wherein another of the two or more different antibodies is a monoclonal antibody which recognizes a peptide comprising the partial amino acid sequence consisting of amino acids 71 to 75 of the amino acid sequence shown in SEQ ID NO:2.

5. The method according to claim 4, wherein the antibody which recognizes a peptide comprising the partial amino acid sequence consisting of amino acids 71 to 75 of the amino acid sequence shown in SEQ ID NO:2 is produced by hybridoma 2B10 deposited under Accession No. FERM BP-4110.

* * * * *

SEQUENCE LISTING

```
<160> NUMBER OF SEQ ID NOS: 6

<210> SEQ ID NO 1
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 1 gtc ccg ctg cct gcg ggc gga ggg acc gtg ctg acc aag atg tac ccg      48
Val Pro Leu Pro Ala Gly Gly Gly Thr Val Leu Thr Lys Met Tyr Pro
 1               5                  10                  15 cgc ggc aac cac tgg gcg gtg ggg cac tta atg ggg aaa aag agc aca      96
Arg Gly Asn His Trp Ala Val Gly His Leu Met Gly Lys Lys Ser Thr
             20                  25                  30
```

```
ggg gag tct tct tct gtt tct gag aga ggg agc ctg aag cag cag ctg     144
Gly Glu Ser Ser Ser Val Ser Glu Arg Gly Ser Leu Lys Gln Gln Leu
            35                  40                  45 aga gag tac atc agg tgg gaa gaa gct gca agg aat ttg ctg ggt ctc     192
Arg Glu Tyr Ile Arg Trp Glu Glu Ala Ala Arg Asn Leu Leu Gly Leu
        50                  55                  60 ata gaa gca aag gag aac aga aac cac cag cca cct caa ccc aag gcc     240
Ile Glu Ala Lys Glu Asn Arg Asn His Gln Pro Pro Gln Pro Lys Ala
 65                  70                  75                  80 ctg ggc aat cag cag cct tcg tgg gat tca gag gat agc agc aac ttc     288
Leu Gly Asn Gln Gln Pro Ser Trp Asp Ser Glu Asp Ser Ser Asn Phe
                85                  90                  95 aaa gat                                                             294
Lys Asp

<210> SEQ ID NO 2
<211> LENGTH: 98
<212> TYPE: PRT
<213> ORGANISM: Homo sapiens

<400> SEQUENCE: 2

Val Pro Leu Pro Ala Gly Gly Gly Thr Val Leu Thr Lys Met Tyr Pro
 1               5                  10                  15

Arg Gly Asn His Trp Ala Val Gly His Leu Met Gly Lys Lys Ser Thr
            20                  25                  30

Gly Glu Ser Ser Ser Val Ser Glu Arg Gly Ser Leu Lys Gln Gln Leu
        35                  40                  45

Arg Glu Tyr Ile Arg Trp Glu Glu Ala Ala Arg Asn Leu Leu Gly Leu
    50                  55                  60

Ile Glu Ala Lys Glu Asn Arg Asn His Gln Pro Pro Gln Pro Lys Ala
 65                  70                  75                  80

Leu Gly Asn Gln Gln Pro Ser Trp Asp Ser Glu Asp Ser Ser Asn Phe
                85                  90                  95

Lys Asp

<210> SEQ ID NO 3
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(204)

<400> SEQUENCE: 3 agt act ggt gag agc tct tct gtt tct gaa cgt gga tcc ctt aag cag     48
Ser Thr Gly Glu Ser Ser Ser Val Ser Glu Arg Gly Ser Leu Lys Gln
 1               5                  10                  15 cag ctt cgc gaa tac atc cgt tgg gaa gaa gct gct cgt aac ctg cta     96
Gln Leu Arg Glu Tyr Ile Arg Trp Glu Glu Ala Ala Arg Asn Leu Leu
            20                  25                  30 ggc ctg atc gaa gct aaa gaa aac cgt aac cac cag ccg ccg cag ccg     144
Gly Leu Ile Glu Ala Lys Glu Asn Arg Asn His Gln Pro Pro Gln Pro
        35                  40                  45 aaa gct tta ggt aac cag cag ccg tct tgg gac tct gaa gac tct tcg     192
Lys Ala Leu Gly Asn Gln Gln Pro Ser Trp Asp Ser Glu Asp Ser Ser
    50                  55                  60 aac ttt aaa gac                                                     204
Asn Phe Lys Asp
 65
```

```
<210> SEQ ID NO 4
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Thr Gly Glu Ser Ser Val Ser Glu Arg Gly Ser Leu Lys Gln
 1               5                  10                  15

Gln Leu Arg Glu Tyr Ile Arg Trp Glu Ala Ala Arg Asn Leu Leu
                20                  25                  30

Gly Leu Ile Glu Ala Lys Glu Asn Arg Asn His Gln Pro Pro Gln Pro
            35                  40                  45

Lys Ala Leu Gly Asn Gln Gln Pro Ser Trp Asp Ser Glu Asp Ser Ser
        50                  55                  60

Asn Phe Lys Asp
 65

<210> SEQ ID NO 5
<211> LENGTH: 8
<212> TYPE: PRT
<213> ORGANISM: Homo sapiens

<400> SEQUENCE: 5

Asn His Gln Pro Pro Gln Pro Lys
 1               5

<210> SEQ ID NO 6
<211> LENGTH: 5
<212> TYPE: PRT
<213> ORGANISM: Homo sapiens

<400> SEQUENCE: 6

Ser Val Ser Glu Arg
 1               5
```